(12) United States Patent
Hsiao (10) Patent No.: US 11,291,461 B2
(45) Date of Patent: Apr. 5, 2022

(54) TOURNIQUET DEVICE

(71) Applicant: DE XING MEDICAL TREATMENT AND INSTRUMENT CO., LTD., Kaohsiung (TW)

(72) Inventor: Te-Hsin Hsiao, Kaohsiung (TW)

(73) Assignee: DE XING MEDICAL TREATMENT AND INSTRUMENT CO., LTD., Kaohsiung (TW)

( * ) Notice: Subject to any disclaimer, the term of this patent is extended or adjusted under 35 U.S.C. 154(b) by 78 days.

(21) Appl. No.: 16/987,415

(22) Filed: Aug. 7, 2020

(65) Prior Publication Data

US 2022/0039805 A1    Feb. 10, 2022

(51) Int. Cl.
*A61B 17/132* (2006.01)
*A61B 17/00* (2006.01)

(52) U.S. Cl.
CPC ............... *A61B 17/1327* (2013.01); *A61B 2017/00367* (2013.01)

(58) Field of Classification Search
CPC .............. A61B 17/132; A61B 17/1322; A61B 17/1327
See application file for complete search history.

(56) References Cited

U.S. PATENT DOCUMENTS

| 1,279,784 | A | * | 9/1918 | Stapler | A61B 17/1327 606/203 |
| 1,569,131 | A | * | 1/1926 | Nord | A61B 17/1327 606/203 |
| 2,604,098 | A | * | 7/1952 | Kranc | A61B 17/1327 606/203 |
| 3,492,995 | A | * | 2/1970 | Ceravolo | A61B 17/1327 606/203 |
| 7,582,102 | B2 | * | 9/2009 | Heinz | A61B 17/1327 606/203 |
| 9,844,385 | B2 | * | 12/2017 | Dickinson | A61B 17/1322 |
| 10,478,196 | B2 | * | 11/2019 | Maris | A61B 17/135 |
| 10,695,071 | B2 | * | 6/2020 | Ward | A61B 17/1325 |
| 10,918,394 | B2 | * | 2/2021 | Searfoss | A61B 17/1327 |
| 2005/0267518 | A1 | * | 12/2005 | Wright | A61B 17/1327 606/203 |
| 2012/0150215 | A1 | * | 6/2012 | Donald | A61B 17/1327 606/203 |
| 2015/0051638 | A1 | * | 2/2015 | Dickinson | A61B 17/1322 606/203 |
| 2016/0095605 | A1 | * | 4/2016 | Maris | A61B 17/1327 606/201 |

(Continued)

*Primary Examiner* — Ryan J. Severson
(74) *Attorney, Agent, or Firm* — Leong C. Lei (57) ABSTRACT

The tourniquet device includes a pressure plate, a winding rod, a control rod, a dial, a locking rod, and a strap. The winding rod and has a ratchet at one end. A ratchet is provided around a bottom end of the control rod engaging the ratchet of the winding rod. The dial is fixedly joined to the control rod, and locking holes are provided on the bottom side of the dial. The locking rod is for locking the dial. The strap has a first end fixedly connected to a buckle and a second end threaded through the slits of the pressure plate and then through the buckle and back. A fastener patch is attached to the strap, and a tightening band has a first end fixedly joined to the strap between the buckle and the fastener patch and a second end is threaded through the slit of the winding rod.

8 Claims, 7 Drawing Sheets

(56) References Cited

U.S. PATENT DOCUMENTS

| | | | |
|---|---|---|---|
| 2017/0100131 A1* | 4/2017 | Olbu | A61B 17/1327 |
| 2018/0193030 A1* | 7/2018 | Ward | A61B 17/1325 |
| 2018/0271541 A1* | 9/2018 | Figueiredo | A61B 17/1327 |
| 2019/0021744 A1* | 1/2019 | Will | A61B 17/1327 |
| 2020/0113579 A1* | 4/2020 | Searfoss | A61B 17/1327 |
| 2020/0367909 A1* | 11/2020 | Rankins, III | A61B 17/1325 |
| 2021/0145454 A1* | 5/2021 | Zhu | A61B 17/1325 |
| 2021/0275191 A1* | 9/2021 | Ward | A61B 17/1327 |

* cited by examiner

TOURNIQUET DEVICE

BACKGROUND OF THE INVENTION

(a) Technical Field of the Invention

The present invention is generally related to tourniquets, and more particular to pressurized tourniquet device.

(b) Description of the Prior Art

Conventional tourniquets usually involve a strap wrapping around a limb between a wound and the heart for applying pressure to stop bleeding.

These conventional tourniquets are usually effective to smaller wounds, but not to larger wounds.

There are so called combat tourniquets that are applicable to larger wounds and more severe bleeding. One example is Taiwan Patent No. M551906 whose teaching includes a plate, a twisting rod, a first strap, and a second strap. The first strap is wrapped around a limb between the wound and the heart and fastened to preliminarily stanch bleeding. The twisting rod is then engaged to pull the first strap and second strap and a locking element fixes the twisting rod to additionally stanch bleeding. The first strap and second strap have to repeatedly run through slits on the plate, the twisting rod, and a fastener. The assembly of the combat tourniquet is therefore rather inconvenient. Especially, the first strap and second strap are twisted and the smoothness of their fastening is compromised. As such, the first strap or second strap is often stuck in a flurry during an emergency, endangering the life of the wounded. Furthermore, the twisting rod cannot be fixed during its application and the first strap and second strap are loosed once the twisting rod is not held firmly, thereby failing to stanch bleeding.

Therefore, there are several shortcomings of the conventional tourniquets' manufacturing and usage, and these shortcomings put the life of a wounded person at stake.

SUMMARY OF THE INVENTION

A novel tourniquet device is provided herein so as to obviate the above-mentioned shortcomings.

The tourniquet device includes a pressure plate, a winding rod, a control rod, a dial, a locking rod, and a strap. The pressure plate includes a first case and a second case respectively sealed by a first cap and a second cap. Two slits are oppositely provided respectively along a front edge and a back edge of the pressure plate between the first and second cases. A pedestal is provided on a lateral outer wall of the second case, and a frame is provided on a lateral outer wall of the second cap corresponding to the pedestal. The winding rod is laterally positioned between the first and second cases, and has a ratchet at one end and a slit axially along an outer circumference of the winding rod. The control rod is positioned between the second case and the second cap. A ratchet is provided around a bottom end of the control rod whose teeth engage those of the ratchet of the winding rod, and a top end of the control rod is extended through and beyond a top side of the second cap. The dial has a bottom side fixedly joined to a top end of the control rod, and a plurality of locking holes provided on the bottom side of the dial. The locking rod has a bottom end plugged into the pedestal of the second case and a top end extended outside the frame of the second cap. A lateral pin is extended horizontally from a middle section of the locking rod. The strap has a first end fixedly connected to a buckle and a second end threaded through the slits of the pressure plate and then through the buckle and back. A fastener patch is attached to the strap, and a tightening band has a first end fixedly joined to the strap between the buckle and the fastener patch and a second end is threaded through the slit of the winding rod.

To apply the tourniquet device, first the pressure plate is positioned on the limb between the wound and the heart. Then, the second end of the strap is wrapped around the limb, through the buckle and back to attach on the strap so that the fastener patch joins to itself for preliminarily stanching. The dial is further turned to engage the control rod. Through the ratchets, the winding rod is turned to pull the tightening band of the strap so that the tightening band is wound around the winding rod to further tighten the strap and to exert further stanching. The lateral pin of the locking rod is moved out of a lower slot opening so that the locking rod rises upward into a locking hole under the dial to prevent the control rod and winding rod from being turned back and to maintain the tightening status of the strap.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
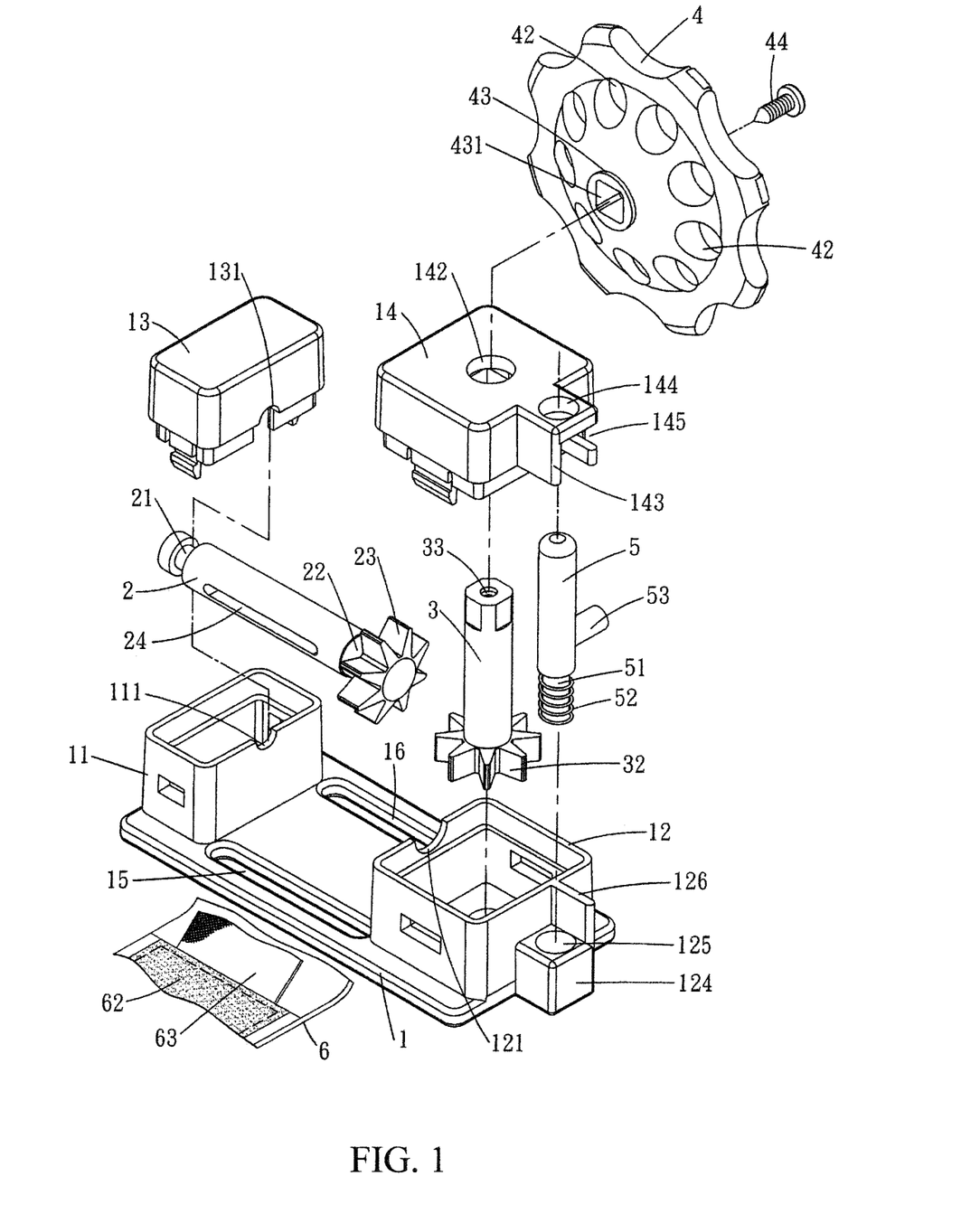
FIG. 1 is a perspective break-down diagram showing a tourniquet device according to an embodiment of the present invention.
Figure 2:
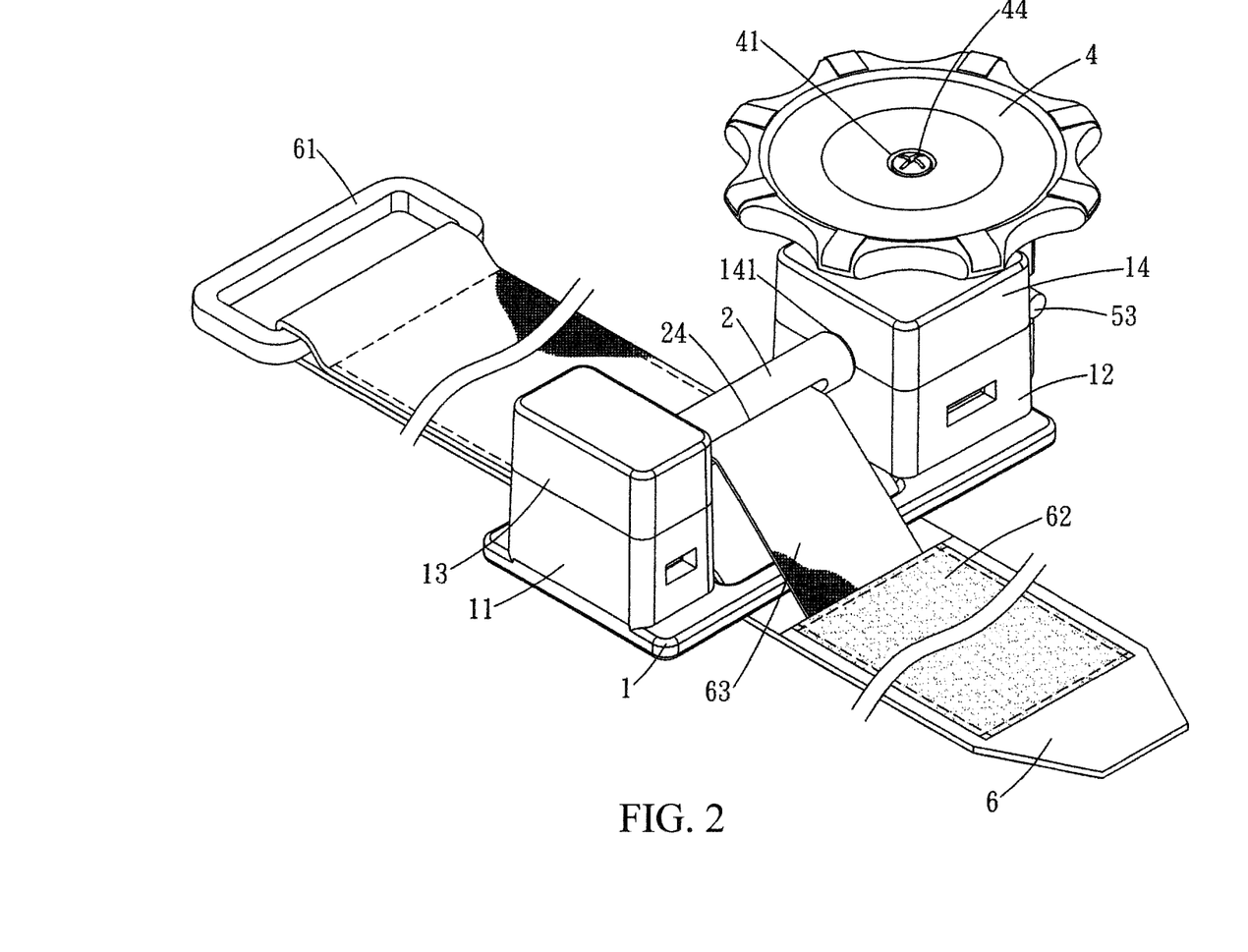
FIG. 2 is a perspective diagram showing the tourniquet device of FIG. 1.

As shown in FIG. 1 and FIG. 2, a tourniquet device according to an embodiment of the present invention includes a pressure plate 1, a winding rod 2, a control rod 3, a dial 4, a locking rod 5, and a strap 6.

Figure 3:
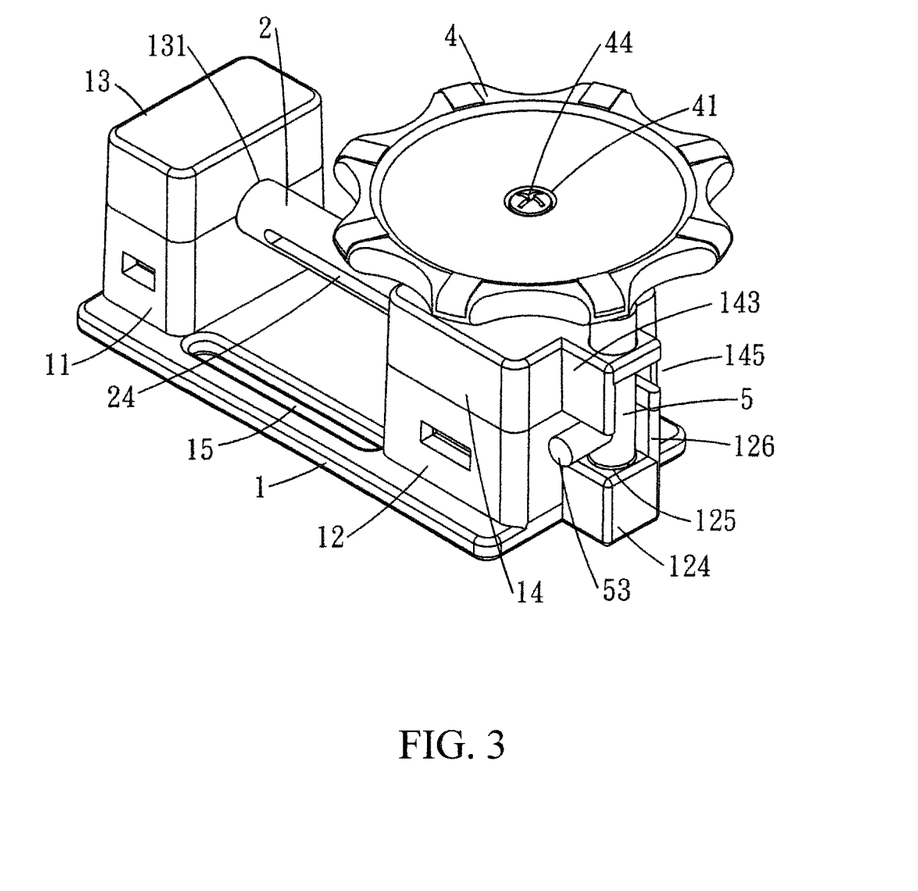
FIG. 3 is a perspective diagram showing the tourniquet device of FIG. 1 without a strap.
Figure 4:
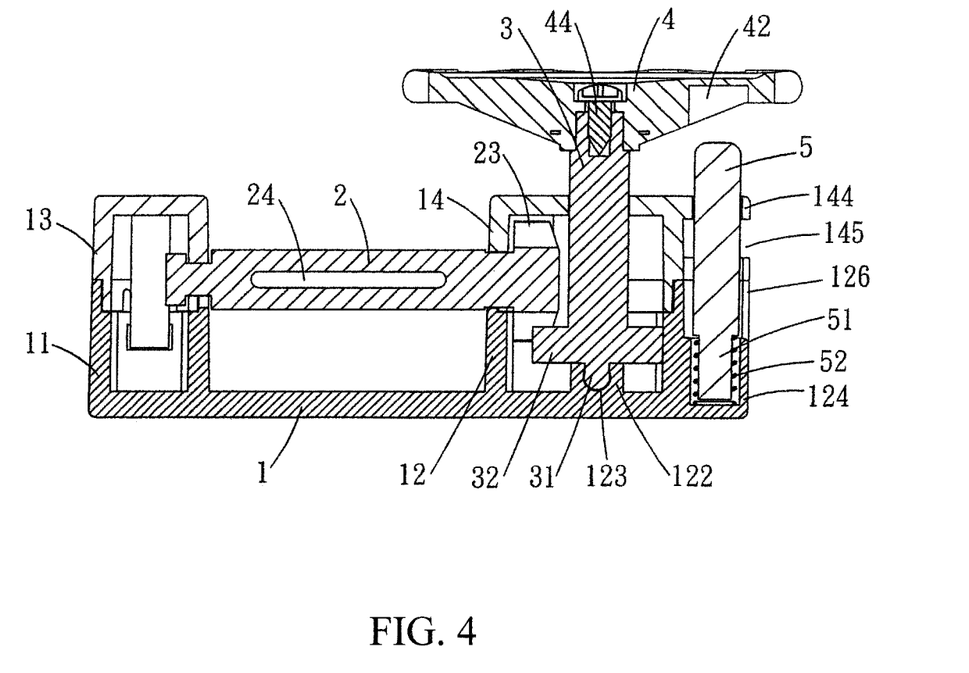
FIG. 4 is a sectional diagram showing the tourniquet device of FIG. 3.

As shown in FIG. 3 and FIG. 4, the pressure plate 1 has an integrally formed body with a planar bottom surface for placing flatly on the surface of a patient's limb. A first case 11 and a second case 12 are respectively provided on two ends of a top surface of the pressure plate 1. Both cases 11 and 12 are open-topped and sealed respectively by a first cap 13 and a second cap 14, thereby forming a space therewithin. Both cases 11 and 12 respectively have semicircular notches 111 and 121 along top edges of their oppositely facing side walls. Correspondingly, both caps 13 and 14 respectively have semicircular notches 131 and 141 along bottom edges of their oppositely facing side walls. When the caps 13 and 14 are joined to the cases 11 and 12, respectively, the notches 111 and 131, and the notches 121 and 141 jointly form circular through openings. A protrusion 122 is provided on a bottom side of the second case 12 protruding into its space. An indentation 123 is formed on at a top end of the protrusion 122. Correspondingly, the second cap 14 has a through opening 142 on a top side that, when the second cap 14 is joined to the second case 12, the through opening 142 and the indentation 123 are aligned vertically.

Figure 5:
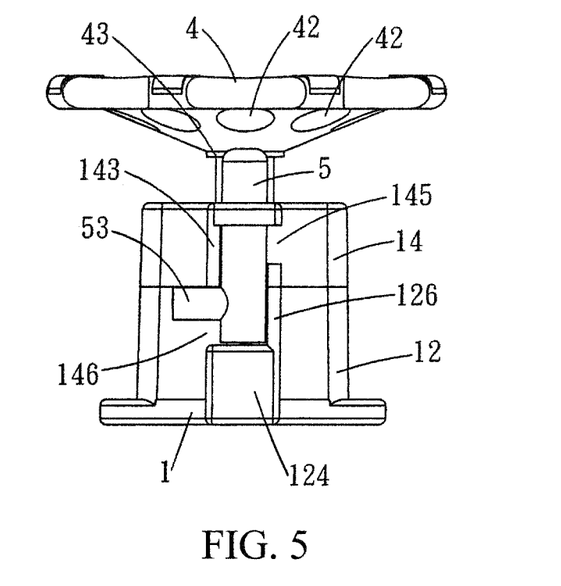
FIG. 5 is a sectional diagram showing the tourniquet device of FIG. 3. when a dial is in a rotatable position.
Figure 6:
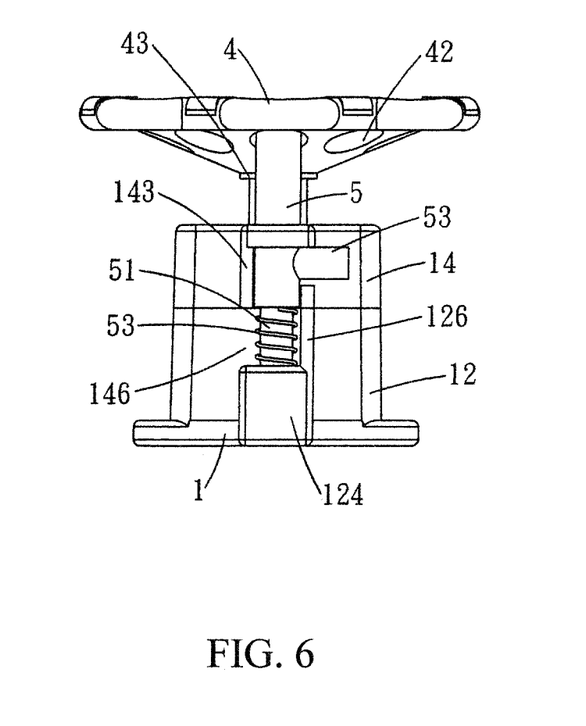
FIG. 6 is a sectional diagram showing the tourniquet device of FIG. 3. when a dial is in a locked position.

A pedestal 124 is provided on a lateral outer wall of the second case 12 whose height is lower than that of the second case 12. A top side of the pedestal 124 has a hole 125 and a back wall 126 is extended upward from a back side of the pedestal 124. A top edge of the back wall 126 is level with that of the second case 12. Corresponding to the pedestal 124, an L-shaped frame is provided on a lateral outer wall of the second cap 14. The frame has a vertical front wall 143 and a through hole 144 on a lateral wall. When the second cap 14 is joined to the second case 12, the through hole 144 is vertically aligned with the hole 125 of the pedestal 124, and the front wall 143 is oppositely positioned against the back wall 126. The front wall 143 has a same height as that of the lateral outer wall of the second cap 14. When the second cap 14 is joined to the second case 12, an upper slot opening 145 is formed above the back wall 126 and a lower slot opening 146 is formed beneath the front wall 143, as shown in FIG. 5 and FIG. 6.

Two slits 15 and 16 are oppositely provided respectively along a front edge and a back edge of the pressure plate 1 between the first and second cases 11 and 12.

The winding rod 2 is cylindrically shaped whose two ends respectively have two ring slots 21 and 22. The winding rod 2 is laterally positioned between the first and second cases 11 and 12 so that the ring slots 21 and 22 are respectively embedded in the circular through openings formed by the notches 111 and 131, and the notches 121 and 141 when the caps 13 and 14 are joined to the cases 11 and 12. The winding rod 2 is as such confined by and rotatable between the cases 11 and 12. The winding rod 2 has a ratchet 23 at one end which would be housed in the space enclosed by the second case 12 and the second cap 14. A slit 24 is axially provided along an outer circumference of the winding rod 2 between the first case 11 and the second case 12.

The control rod 3 is cylindrically shaped with a pin 31 axially extended from one end. A front tip of the pin 31 is plugged into the indentation 123 and a ratchet 32 is provided around the pin 31 behind the front tip. The teeth of the ratchet 32 are compatible with and engage those of the ratchet 23. The control rod 3 is as such vertically supported by the protrusion 122 and extended through and beyond the through opening 142 of the second cap 14 for an appropriate length. The control rod 3 then may be turned and the winding rod 2 is also engaged to spin. A top end of the control rod 3 is cubically shaped with a socket 33 on a top side.

The dial 4 has a disc shape with wave-like circumference. The dial 4 has a flat top side and a downward bulge on a bottom side. A number of locking holes 42 are arranged at intervals on and around the bulge. A bolt hole 41 is provided in the center of the top side. A protrusion 43 is provided in the center of the bulge with a rectangular opening 431 connecting with the bolt hole 41. The protrusion 43 is plugged into the through opening 142 of the second cap 14. The rectangular opening 431 is for receiving the top end of the control rod 3. A bolt 44 is run through the bolt hole 41 of the dial 4 and into the socket 33 at the top end of the control rod 3. The dial 4 is as such fixedly joined to the control rod 3 so that, when the dial 4 is turned, the control rod 3, along with the winding rod 2 is engaged to turn. When the dial 4 is turned, the locking holes 42 would be respectively aligned with the through hole 144 of the second cap 14.

The locking rod 5 is also cylindrically shaped whose lower section 51 has a smaller diameter and is threaded through a spring 52. The lower section 51, along with the spring 52, is plugged into the hole 125 on the pedestal 124 of the second case 12. An upper section of the locking rod 5 runs through the through hole 144 of the second cap 14 for an appropriate length so that it may be received by or retracted from one of the locking holes 42 on the bottom side of the dial 4 through the spring 52. A lateral pin 53 is extended horizontally from a middle section of the locking rod 5. The lateral pin 53 prevents the locking rod 5 from escaping from the through hole 144. When the locking rod is pressed downward and the spring 52 is compressed, the lateral pin 53 may be turned into the lower slot opening 146 between the front wall 143 and the pedestal 124 to overcome the expansion of the spring 52, and the locking rod 5 is as such positioned to remain detached from the dial 4. As shown in FIG. 5, the dial 4 is then freely rotatable. When the lateral pin 53 is turned and leaves the lower slot opening 146, the expansion of the spring 52 then raises the locking rod 5 upward so that it is plugged into one of the locking holes 42 to lock and prevent the dial 4 from turning. As such, the control rod 3 and winding rod 2 are locked as well. As shown in FIG. 6, the lateral pin 53 may be further turned into the upper slot opening 145 so as to lock the dial 4 reliably and to prevent the lateral pin 53 from being mistakenly turned.

Figure 7:
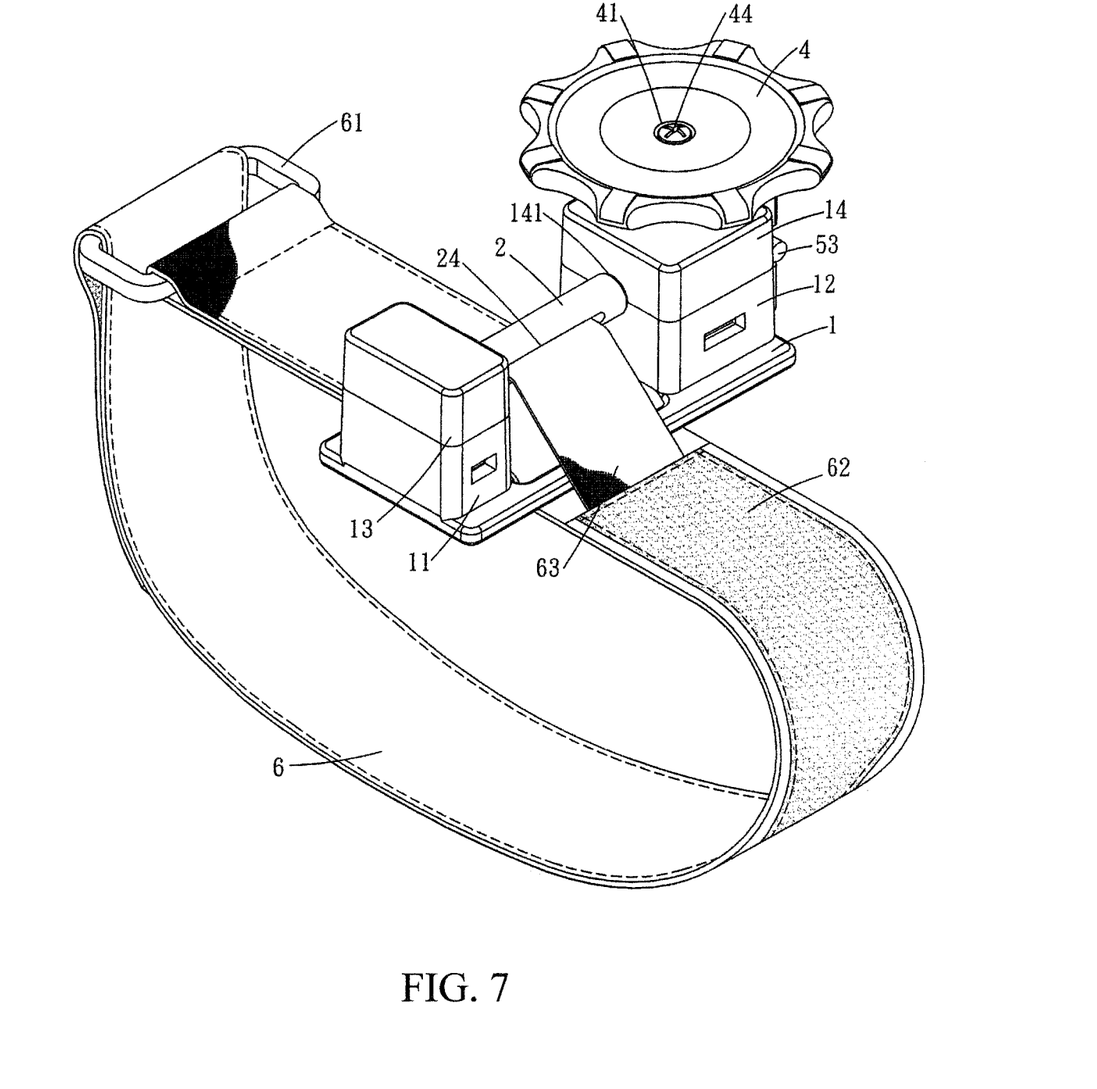
FIG. 7 shows an application scenario of the tourniquet device of FIG. 1.
Figure 8:
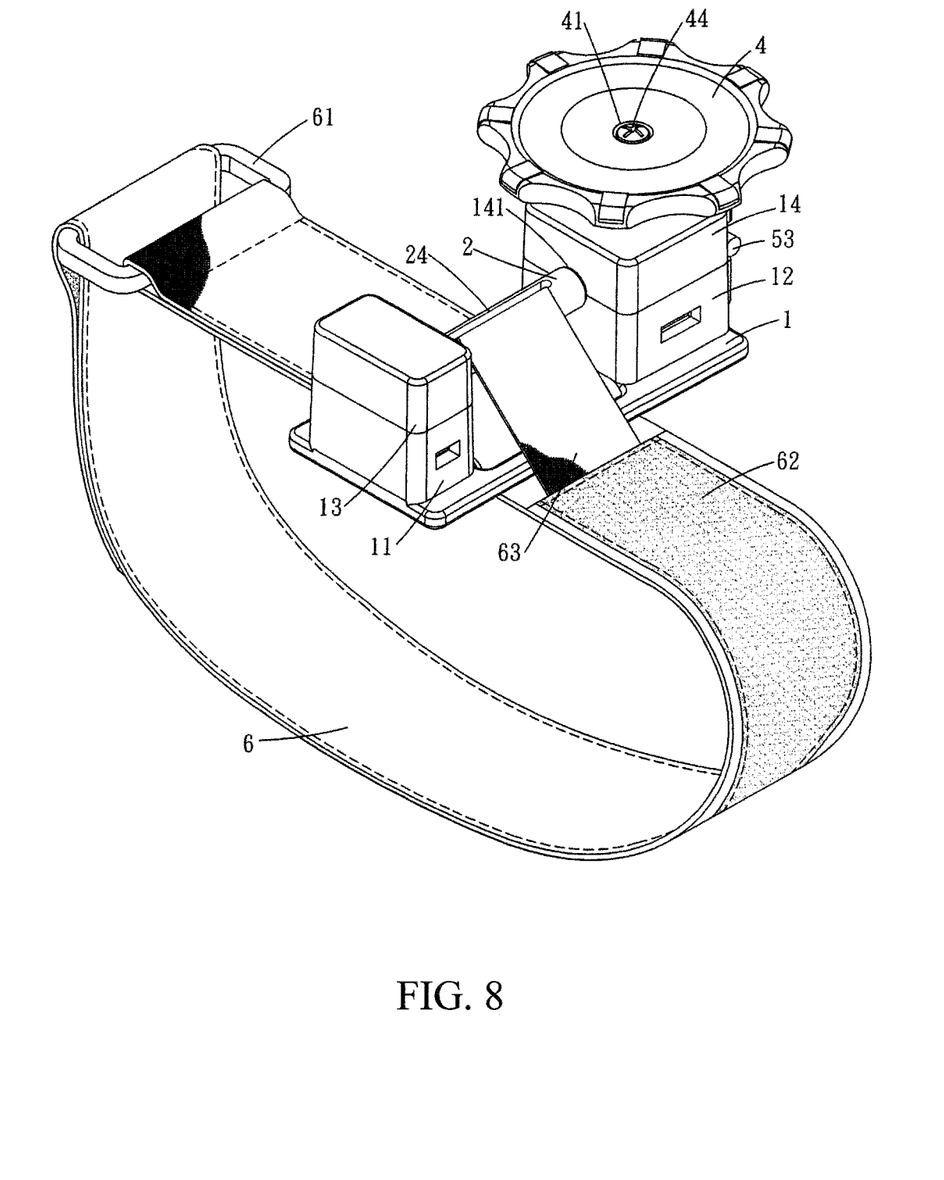
FIG. 8 shows another application scenario of the tourniquet device of FIG. 1.

The strap 6 is made of a flexible and robust material, and has a width compatible with that of the slits 15 and 16 of the pressure plate 1. A first end of the strap 6 is fixedly connected to a buckle 61. A second end of the strap 6 is threaded through the slit 15 from below, then through the slit 16 from above, and then through the buckle 61 and back. A fastener patch 62 is sewed along its two long edges on an outer surface of the strap 6, leaving a space between the fastener patch 62 and the strap 6. The second end of the strap 6, after threading through the buckle 61, may be attached to the strap 6 by the fastener patch 62. As such, the strap 6 may be wrapped around the limb of a wounded person and tightened to preliminarily stanch bleeding, as shown in FIG. 7. A tightening band 63 has a first end fixedly joined to the strap 6 between the buckle 61 and the fastener patch 62, and a second end is threaded through the slit 24 of the winding rod 2 and extended into the space between the strap 6 and the fastener patch 62 for an appropriate length. The second end of the tightening band 63 is then sewed and fixed. Then, by turning the winding rod 2, the tightening band 63 is pulled from the space and around the winding rod 2 to provide additional constriction on the strap 6 to further stanch bleeding, as shown in FIG. 8.

To apply the tourniquet device, first the pressure plate 1 is positioned on the limb between the wound and the heart. Then, the second end of the strap 6 is wrapped around the limb, through the buckle 61 and back to attach on the strap 6 so that the fastener patch 62 joins to itself for preliminarily stanching. The dial 4 is further turned to engage the control rod 3. Through the ratchets 32 and 23, the winding rod 2 is turned to pull the tightening band 63 of the strap 6 so that the tightening band 63 is wound around the winding rod 2 to further tighten the strap 6 and to exert further stanching. When the dial 4 cannot be further turned, the lateral pin 53 of the locking rod 5 is moved out of the lower slot opening 146 so that the locking rod 5, under the resilience of the spring 53, rises upward into a locking hole 42 under the dial 4 to prevent the control rod 3 and winding rod 2 from being turned back and to maintain the tightening status of the strap 6. The lateral pin 53 is then further moved into the upper slot opening 145 to reliably lock the dial 4 and the wound may be further processed.

As described above, by simply pulling the strap 6 and turning the dial 4, together with the locking by the lateral pin 53, the bleeding from the wound may be stanched. The tourniquet device as such provides convenient operation and effective stanching so that the wound may be taken care properly.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A tourniquet device, comprising:
   a pressure plate, where the pressure plate comprises a first case and a second case respectively sealed by a first cap and a second cap, two slits are oppositely provided respectively along a front edge and a back edge of the pressure plate between the first and second cases, a pedestal is provided on a lateral outer wall of the second case, and a frame is provided on a lateral outer wall of the second cap corresponding to the pedestal;
   a winding rod laterally positioned between the first and second cases, where the winding rod has a ratchet at one end and a slit axially along an outer circumference of the winding rod;
   a control rod positioned between the second case and the second cap, where a ratchet is provided around a bottom end of the control rod whose teeth engage those of the ratchet of the winding rod, and a top end of the control rod is extended through and beyond a top side of the second cap;
   a dial, where a bottom side of the dial is fixedly joined to a top end of the control rod, and a plurality of locking holes are provided on the bottom side;
   a locking rod whose bottom end is plugged into the pedestal of the second case and top end is extended outside the frame of the second cap, where a lateral pin is extended horizontally from a middle section of the locking rod; and
   a strap, where a first end of the strap is fixedly connected to a buckle, a second end of the strap is threaded through the slits of the pressure plate and then through the buckle and back; a fastener patch is attached to the strap; and a tightening band has a first end fixedly joined to the strap between the buckle and the fastener patch and a second end is threaded through the slit of the winding rod.

2. The tourniquet device according to claim 1, wherein the cases respectively have semi-circular notches along top edges of their oppositely facing side walls; both caps respectively have semi-circular notches along bottom edges of their oppositely facing side walls; when the caps are joined to the cases, respectively, the notches of the cases and the notches of the caps jointly form circular through openings; the winding rod's two ends respectively have two ring slots; and the ring slots are respectively embedded in the circular through openings.

3. The tourniquet device according to claim 1, wherein a protrusion is provided on a bottom side of the second case; an indentation is formed on at a top end of the protrusion; the second cap has a through opening on a top side that, when the second cap is joined to the second case, the through opening and the indentation are aligned vertically; the control rod has a pin axially extended from one end; a front tip of the pin is plugged into the indentation; and the control rod is extended from the protrusion through and beyond the through opening of the second cap.

4. The tourniquet device according to claim 1, wherein the dial has a downward bulge on a bottom side; and the locking holes are arranged at intervals on and around the bulge.

5. The tourniquet device according to claim 1, wherein a top side of the pedestal has a hole; the frame has a through hole on a lateral wall; when the second cap is joined to the second case, the through hole is vertically aligned with the hole of the pedestal; the locking rod has a lower section of a smaller diameter threaded through a spring; the lower section, along with the spring, is plugged into the hole on the pedestal of the second case; an upper section of the locking rod runs through the through hole of the second cap so that it is selectively received by or retracted from one of the locking holes.

6. The tourniquet device according to claim 5, wherein a back wall is extended upward from a back side of the pedestal; a top edge of the back wall is level with that of the second case; the frame has a vertical front wall; when the second cap is joined to the second case, the front wall is oppositely positioned against the back wall, an upper slot opening is formed above the back wall and a lower slot opening is formed beneath the front wall; and the lateral pin is selectively positioned in one of the upper and lower slot openings.

7. The tourniquet device according to claim 1, wherein a back wall is extended upward from a back side of the pedestal; a top edge of the back wall is level with that of the second case; the frame has a vertical front wall; when the second cap is joined to the second case, the front wall is oppositely positioned against the back wall, an upper slot opening is formed above the back wall and a lower slot opening is formed beneath the front wall; and the lateral pin is selectively positioned in one of the upper and lower slot openings.

8. The tourniquet device according to claim 1, wherein the fastener patch is sewed along its two long edges on an outer surface of the strap, leaving a space between the fastener patch and the strap; the tightening band has the second end extended into the space between the strap and the fastener patch; and the second end of the tightening band is sewed and fixed to the strap.

\* \* \* \* \*